128-24A   AU 335   EX
3/9/76    OR   3,942,519

United States Patent [19]
Shock

[11] 3,942,519
[45] Mar. 9, 1976

[54] METHOD OF ULTRASONIC CRYOGENIC CATARACT REMOVAL

[75] Inventor: John P. Shock, San Rafael, Calif.

[73] Assignee: Ultrasonic Systems, Inc., Farmingdale, N.Y.

[22] Filed: Aug. 12, 1974

[21] Appl. No.: 496,565

Related U.S. Application Data

[63] Continuation-in-part of Ser. No. 318,429, Dec. 26, 1972, Pat. No. 3,857,387.

[52] U.S. Cl. ............................ 128/24 A; 128/303.1
[51] Int. Cl.² ...................... A61F 9/00; A61B 17/36
[58] Field of Search ....................... 128/24 A, 303.1

[56] References Cited
UNITED STATES PATENTS

| | | | |
|---|---|---|---|
| 3,439,680 | 4/1969 | Thomas, Jr. | 128/303.1 |
| 3,451,395 | 6/1969 | Thyberg | 128/303.1 |
| 3,589,363 | 6/1971 | Banko | 128/24 A X |
| 3,736,938 | 6/1973 | Evvard et al. | 128/24 A X |
| 3,812,855 | 5/1974 | Banko | 128/24 A X |

*Primary Examiner*—Channing L. Pace

[57] ABSTRACT

Ultrasonic and cryogenic instrumentation for the removal of unwanted tissue material from an animal, such as a human, and more particularly, adapted for the removal of cataracts, in surgical operations. The ultrasonic and cryogenic instrumentation include hand-held instruments with the cryogenic instrumentation adapted to first freeze the cataract lens and after the cataract lens has unfrozen the ultrasonic instrumentation is adapted by a vibrating tool to reduce the volume of the cataract and thereafter, through the simultaneous introduction of a fluid and creating a flow, the cataract mass exits through the incision around the vibrating tool until all of the unwanted tissue forming the cataract lens is removed.

59 Claims, 18 Drawing Figures

METHOD OF ULTRASONIC CRYOGENIC CATARACT REMOVAL

CROSS-REFERENCE TO RELATED APPLICATION

This application is a continuation-in-part of my co-pending patent application, Ser. No. 318,429, filed Dec. 26, 1972, now U.S. Pat. No. 3,857,387, issued Dec. 31, 1974, for Ultrasonic Cataract Removal Method and Apparatus, which entire subject matter of the co-pending application is incorporated herein by reference as if fully herein set forth.

BACKGROUND OF THE INVENTION

The present invention relates broadly to surgical procedures for animals and more particularly, for the removal of cataracts with the interrelated combined use of ultrasonic and cryogenic instrumentation.

DISCUSSION OF THE PRIOR ART

Prior to the development of the present invention, certain operating procedures have been developed for the removal of cataracts using either cryogenics or ultrasonic energy, but not the combination of the two procedures. The cryogenic techniques for use in cataract removal are known today and are utilized to freeze the lens into a solid mass to permit this frozen mass to be gripped and removed as a complete structure from its containment within the eye. This procedure uses cryogenics to obtain a freezing of the mass to be removed and the technique is practiced with the lens mass in its frozen condition since the purpose is to have means for gripping the lens which in its unfrozen condition would either fracture upon being gripped with a surgical instrument or could not be removed as a complete entity.

Applicant has now discovered a new and novel application of cryogenics in that by freezing and thereafter permitting a defrosting of the lens to occur that internal changes in the character of the lens does occur which enhances the ultrasonic procedure as hereinafter discussed in detail. Accordingly, in contrast to the teaching of the prior art, applicant is using cryogenics in a new and novel way to change the character of the lens prior to removal.

Further, the ultrasonic procedure known today, as disclosed in U.S. Pat. No. 3,589,363, includes a process for the removal of cataracts by emulsifying the lens with an ultrasonic probe requiring aspiration of the emulsified material. Because aspiration is a required aspect of the procedure, it is necessary to have complex electronic and hydraulic equipment for delicate control of inflow and outflow in the eye. This complex equipment requires a trained technician to operate other than the operator and is quite expensive to manufacture.

In view of the above, it is obviously apparent that the ultrasonic surgical procedure as disclosed in the abovereferenced patent requires a complexity of interacting steps having a balance to each other that must be performed in order to have a successful surgical procedure. Furthermore, due to the complexity of the equipment, the surgeon is therefore dependent upon a skilled technician who must be likewise trained and made available for each operation. This, in addition to other factors, would increase the cost per operation and the availability of the equipment to ophthalmologists who might not have a large cataract practice.

In the prior art procedure, a tip in the form of a hollow tube, which is subjected to ultrasonic vibration, is surrounded by a plastic tube which is not subjected to vibration. This combined system is inserted into the anterior chamber of the eye through a small incision and provision is made for hydrodynamic flow both in the area between the two above-indicated tubes and within the interior of the vibrating tube. It is of the greatest importance that a proper balance be established between the two flows referenced to. The first flow is a gravity flow of liquid into the anterior chamber. The second flow is the result of a suction of liquid out of the chamber through the interior of the hollow vibrating tube. It is essential that these two flows be balanced so that there is neither an excessive build-up of pressure in the anterior chamber or a reduction in pressure which could cause a collapse of the anterior chamber.

In order to achieve this sensitive and delicate balance, the prior art found it necessary to develop a very complex electro-hydraulic means with a series of failsafe devices in order to accomplish this result. Furthermore, there is no other provision made to guarantee that every particle of dispersed cataract material is aspirated before making some orbit in the anterior chamber. In other words, for example, if a population of 100,000 small particles were created by the ultrasonic emulsifier, these particles are created in the presence of an inflowing stream of liquid combined with an adjacent rapidly outflowing stream of liquid. The hydrodynamic circulation in the anterior chamber under these circumstances would allow for the movement in the anterior chamber of those few particles which might accidentally escape from time to time during the operation.

In the case of hard cataracts, these particles could very well have an abrasive character if they were to slide past in contact with the walls of the chamber. In the case of the endothelium of the cornea which forms a part of this chamber, there is extreme sensitivity to any such abrasion and must be avoided at all costs Another feature of the prior art is that the aspiration requires very careful manipulation of the tip by the surgeon to prevent aspirating other than cataract material.

OBJECTS OF THE INVENTION

An object of the present invention is to provide an improved method and apparatus for progressively removing a mass of tissue from a human or other animal.

Another object of the present invention is to provide an improved method and apparatus for removing cataracts having different grades of hardness.

Another object of the present invention is to provide a method and apparatus for selectively fracturing and removing layers of living organic tissue from a biological organism.

Another object of the present invention is to provide a method and apparatus for the removal of living organic tissue from a cataract in a rapid manner and with the exertion of a minimum of physical energy by the surgeon affecting such removal.

Another object of the present invention is to provide an improved method and apparatus for softening of the cataract lens, to facilitate removal thereof and to reduce trauma to posterior capsule and cornea of the eye.

Another object of the present invention is to provide an improved method of cataract removal by combining cyrogenic and ultrasonic techniques.

Another object of the present invention is to provide an improved method for softening the lens material of a cataract lens.

Another object of the present invention is to provide an improved means of cataract removal wherein the hard cataract lens if softened by first freezing and subsequently defrosting the cataract.

Other objects and advantages of this invention will become apparent as the disclosure proceeds.

SUMMARY OF THE INVENTION

Accordingly, in light of the prior art problems and after study of the method, applicant's own procedure as described herein was developed. From applicant's own experience, it was evident that removal of soft cataracts through a small incision, hollow tube technique, without vibration worked well with a very modest flow rate (of the order of 1cc per second) and that the lavage or wash-out took place without damage to the walls of the anterior chamber, particularly the endothluim. To applicant, this was a key factor; namely, to find a means of maintaining such gentle lavage and at the same time safely introduce ultrasonic fragmentation. This compelled applicant in this direction because in the case of harder cataracts, the soft cataract removal method just described is not applicable and applicant's intent was to extend his simple lavage technique.

To this end, by the addition of intermittent ultrasonic vibration to the tube or tool member used for lavage and by controlling the ultrasonic vibration not to introduce speeds of hydrodynamic flow which would be above the gentle lavage range so that, even if small particles were flowing in the anterior chamber during the irrigation, the danger to the anterior chamber was minimized. The way of assuring this result was simply in the recognition that, when the tool member was vibrated, it was held to a stroke of vibration such that the peak speed of the tool during reciprocation remained also in the lavage range.

It was further recognized that there is a unique quality arising when the tool member vibration gets up in the high frequency range of 5,000 to 500,000 cycles per second which is the frequency range defined herein as the ultrasonic range. This unique feature is that we have simultaneously an invisible microscopic movement combined with a low peak speed of said vibration and a very high acceleration of at least 1000g. This is a unique feature of such frequency vibrations. The high accelerations produced in these low velocity movements provide just the additional dynamic element needed to break up the harder types of cataracts.

The outstanding and unexpected results obtained by the practice of the method and apparatus of the present invention simplifies the operative procedure in order to remove a harder cataract using ultrasonic vibrational energy, as hereinafter explained in detail. It should be understood that this procedure is intended for use for patients where an extracapsular cataract extraction is indicated and who have had hard cataracts.

The surgical procedure in accordance with the present invention is essentially as follows:

The patient is given a local anesthetic which consists of a lid block and a retrobulbar injection. This local anesthetic is all that is generally required for conventional cataract removal procedures; but I might point out that, with the prior art ultrasonic cataract removal procedures to date, a general anesthetic has been given in that, due to the greater delicacy of the operating procedure, it has been more important that there be absolutely no movement of the eye during the operating procedure.

After the anesthetic has been administered, a small limbal or fornix based conjunctival flap is performed. Then an approximate 2mm limbal incision is made into the anterior chamber. The aqueous is generally removed from the anterior chamber and a small amount of air is inserted. A small cystotome is inserted through the incision and the anterior capsule of the lens is removed. If the anterior capsule is not completely withdrawn by the cystotome, then a small pair of capsule forceps can be inserted to complete the removal. If used, the air is removed and normal saline is inserted into the anterior chamber.

At this time a single tunnel is attempted to directly gain access to the nuclear in the case of a suspected hard lens. If the lens is found to be soft, then the technique as set forth in applicants co-pending application Ser. No. 318,429 filed Dec. 26, 1972 now U.S. Pat. No. 3,857,387, issued Dec. 31, 1974, as hereinabove referred to may be continued with to carry out the procedure set forth therein without cryogenics. The tunnel may be formed by using the needle vibrated ultrasonically or by other means in case of a hard lens in which the cryogenic process in accordance with the present invention is employed.

Accordingly, when the surgical decision predicts a very hard cataract, then the following procedure may first be carried out. Ideally, three tunnels are bored, with the vibrating tip, into the lens nucleus. A 1mm cryoprobe, insulated except for its tip, is inserted into the center tunnel. An ice ball is formed, care being taken that only lens material is frozen. The probe is then defrosted and the cryogenic tip removed. The procedure is then halted for several minutes to allow the hard lens material to absorb or imbibe anterior chamber fluid. This causes the hard material to become soft and resiliant through its uptake of fluid. After this has occurred, the vibrating tip is then reemployed as previously described and the procedure continued.

At this point, the thin walled approximately 19 gauge metallic needle which can be vibrated with ultrasonic energy is reinserted into the anterior chamber through the incision. Prior to the insertion of the needle, a slow drip of physiological saline, or other fluid, is allowed to flow continuously through the needle. This flow of fluid through the needle is accomplished merely by providing a gravity feed flow from an intravenous pole arrangement.

The inventor of the present invention has now discovered, in accordance with the present invention as hereinafter discussed in greater detail, that it is possible to in effect soften a senile or hardened cataract lens by first freezing same and then permitting it to thaw. Although this theory is not completely explainable at this time, applicant has discovered that a change in the hardness of the cataract does take place wherein it is softened relative to its original condition prior to freezing thereof. This reduction in hardness enhances the cataract removal procedure when the ultrasonic vibratory energy is applied. The gravity feed system is more than adequate to permit the input of fluid, maintenance of the anterior chamber, and removal of fragmented material. In view of this fact, no aspiration is required, but rather simple gentle lavage is all that is necessary for the removal of unwanted material.

Having positioned the needle to the cataract while viewing the needle and anterior chamber area through an operating microscope, and with the flow being in proper adjustment, the tip is ultrasonically energized for a short period of time which fragments the material immediately adjacent to the tip. The period during which the tip is energized may vary anywhere from approximately a millisecond to a second, depending upon the speed of foot movement on the foot switch. The surgeon selects the interval of energization to allow complete and perfect control of the operative procedure.

The mass of material forming the cataract to be removed is initially broken into a plurality of fragmented sub-masses or major sections which are each thereafter removed in its entirety or further fragmented into a plurality of particle size masses such that it may exit from the incision with the irrigation fluids. During the surgical procedure, the surgeon initially cross-drills or bores a plurality of apertures into the cataract such as to create a tunneling effect and these cross-bores or apertures are formed by the vibrating ultrasonic member such that a plurality of sub-masses are formed during this aspect of the surgical operation. These sub-masses are thereafter individually either reduced in size or are of an initial size to permit their exiting through the incision around the outer surface of the tool member which is extending through the incision.

In softer cataracts only a small volume of the cataract need be ultrasonically fragmented. This allows the remainder to alter its shape due to the slight hydrostatic pressure differential, and the entire cataract will in a sense flow itself out through the incision.

Accordingly, the tip or output edge of the needlelike tool member is positioned in engagement with the immediate portion of the cataract to be removed, prior to ultrasonically energizing the tip of the needle tool member. Upon energization of the tip of the tool member, a portion of the cataract in surrounding relation thereto is fragmented and the size of the fragmented section is a function of the hardness and nature of the cataract material; for example, the fragments may range from practically invisibility to sections of millimeter dimensions. These fragments, depending upon their size, are lavaged by the continuous stream of irrigation previously described around the vibrating needle and through the original incision site. In those instances where the fragment is too large to flow out the incision site, the ultrasonic needle can be re-applied to it and further fragmented. This process of intermittent engagement and energization of the tip is repeated until such time as the entire cataract is fragmented and removed through the incision by the lavage. This ability to handle such fragmented material is typical of the delicate and accurate control of which this novel procedure is capable.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

DETAILED DESCRIPTION OF THE DRAWINGS

Figure 1:
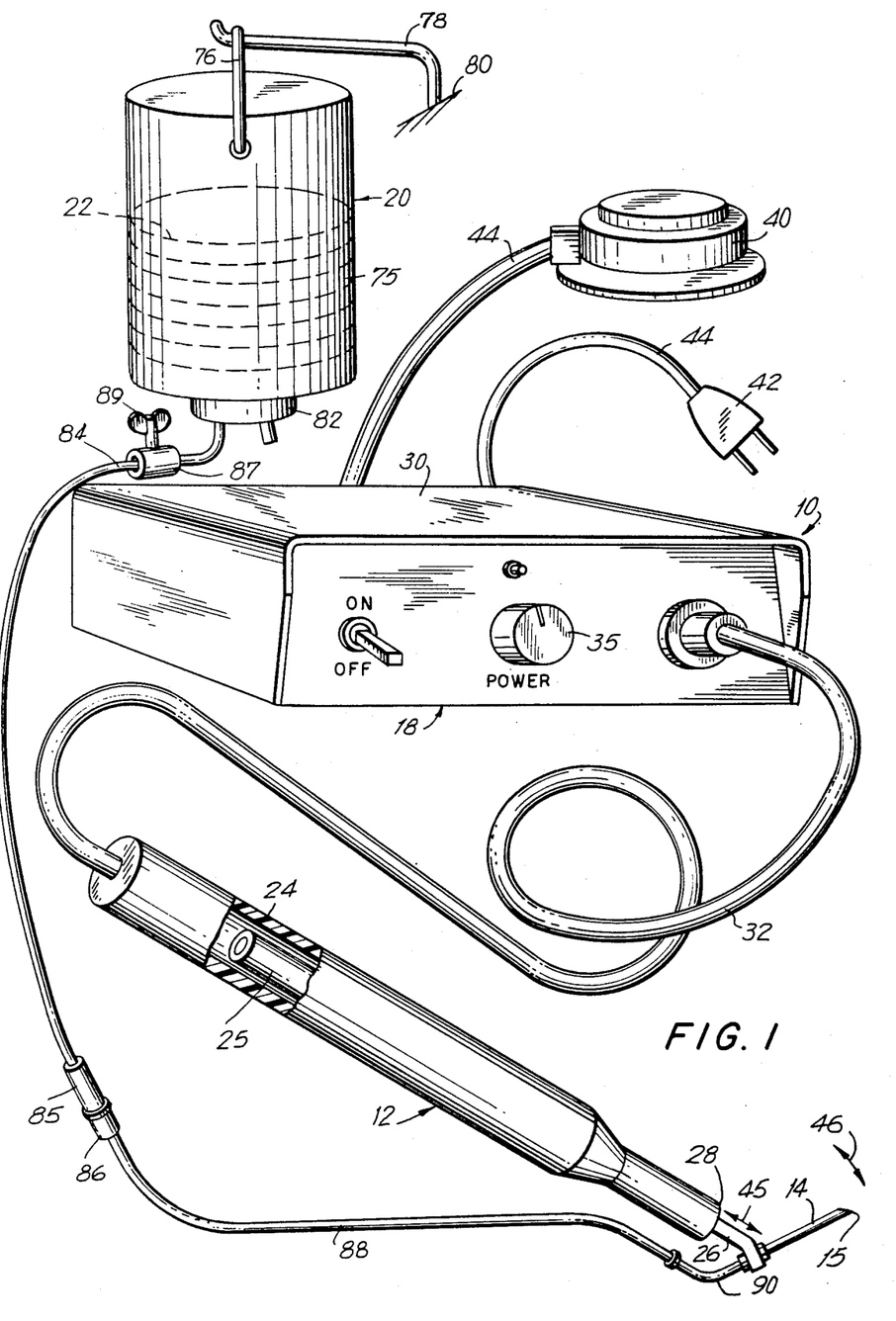
FIG. 1 is a somewhat schematic view of the ultrasonic system for driving a tool member adapted for the surgical procedure claimed herein.
Figure 2:
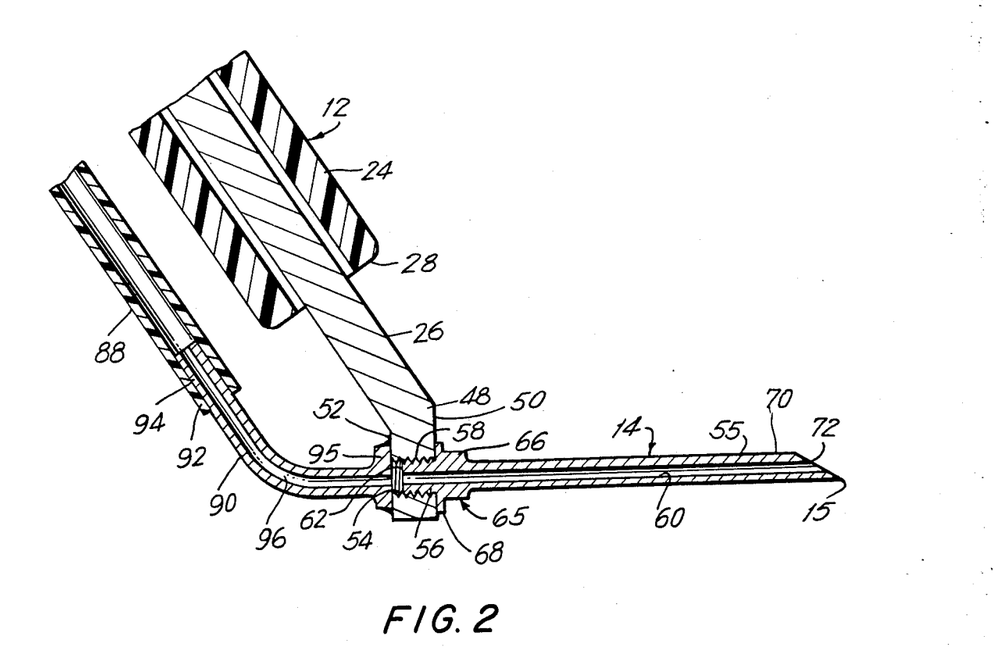
FIG. 2 is an enlarged view in cross-section of the tool member in assembled relation to the ultrasonic system for use herein.

Referring to the drawings in detail and initially to FIGS. 1 and 2 thereof, it will be seen that apparatus 10 for ultrasonically removing a mass such as a cataract from an animal may include instrument means 12 for effecting the necessary high frequency vibrations of the tool member or probe 14 having a relatively sharp output edge or tip 15. Operatively associated with the instrument means 12 is generating means 18 for powering same and fluid supply means 20 for providing a fluid 22 at the operative site. The instrument means 12 may be in the form of a handpiece adapted for being hand held and generally comprising a tubular housing 24 with an ultrasonic motor or transducer 25 being contained therein and having an output end or stem 26 of the motor 25 extending axially beyond the front end 28 of the housing 24 and to which the tool member 14 is coupled. The ultrasonic motor 25 is energized by the generator 18, contained in a cabinet 30 with a power cable 32 connecting the two together. The generator 18 is an oscillator adapted to produce electrical energy having an ultrasonic frequency and contains a shut-off switch 34 and a power control knob 35 with an indicator light 36 on the front panel 38 of the generator 18 to permit the surgeon to properly monitor and adjust the power transmitted to the ultrasonic motor 25.

In conjuction with the generator 18 is a foot switch 40 connected thereto to be used by the surgeon and a plug 42 with a power cable 44 which is plugged into a conventional outlet in order to obtain the necessary electricity for the apparatus 10.

The ultrasonic motor 25 may be one of a variety of electromechanical types such as piezoelectric or magnetostrictive. The ultrasonic motor 25 is designed to operate at a desired frequency generally in the range of 5,000 cycles per second to 500,000 cycles per second, but preferably in the range of 15,000 cycles per second to 100,000 cycles per second and the front output end 26 which is adapted to receive a variety of working tools 15 and wherein each working tool is mechanically coupled to the motor so that it is vibrated at the proper amplitude of vibration.

The transducer of the ultrasonic motor is longitudinally dimensioned so as to have lengths which are whole multiples of half-wavelengths of the waves generated therein such that the exterior working end of the ultrasonic motor is a longitudinal loop of motion as indicated by double headed arrow 45. This longitudinal motion is converted into a lateral motion as indicated by the double headed arrow 46 at the tip 15. The amplitude of longitudinal vibration is generally in the range of 0.0001 to 0.010 and the hyper accelerations exceed 1,000g at the tool tip 15. The design of the output end of the motor 25 and the tool 15 may be designed to either magnify or reduce the amplitude of the vibrations received from the ultrasonic motor 25 and may be designed so as to obtain either longitudinal, elliptical, orbital, flexural, lateral, etc., vibrational modes at the tip.

The tool 15 as seen in FIG. 2 may be in the form that is adapted to be removably secured to the shank end 26 of the instrument means 12 and which is seen to have an angularly disposed base portion 48 with respect to the longitudinally extending shank portion 26 of the ultrasonic motor 25. The base portion 48 has a spaced apart front face surface 50 and a rear face surface 52 with a threaded portion 54 extending therein. For a more detailed discussion of the ultrasonic motor-converter system, reference may be made to U.S. Pat. No. 3,809,977 issued May 7, 1974, for application Ser. No. 119,298, filed Feb. 26, 1971, and assigned to the assignee of the present invention.

The tool 14 may be of a needle-like member having a rear section 56 with a threaded portion 58 adapted to meet with the complimentary threads 54 in the front end 48 and having an axially extending bore 60 extending from its rear end 62 to its front tip 15 to permit a fluid to enter therethrough as hereinafter explained in detail. The tool 14 further includes gripping means 65 in the form of a mid-section 66 which may be of a hexognonal shape to permit its being gripped by an instrument such as a pair of pliers or wrench for proper tightening such that the threaded stud 58 screws into the tapped hole 54 for effecting the rigid connection of the tool 14 to stem 50. A radial flange 68 is integrally formed with the midsection 66 and rear section 56 and abuts the front face 50.

The shaft portion 55 of the tool member 14 is integrally formed with the mid-section 66 and rear section 56 with the bore 60 extending axially there through to provide a fluid passage. The operative tip 14 is preferably formed of an extremely hard, sterilizable material, such as titanium, and for most surgical applications is made of extremely small dimension. Since this is the only portion of the instrument that is brought into contact with the tissue to be broken apart and removed, it will be evident that only a very short incision need to be made in the outer surface to permit access of the tip. The diameter of the outer surface of the shaft portion 55 may be in the range of 0.010 inch to 0.250 inch but is preferably in the range of 0.030 inch to 0.050 inch. The inner bore 60 being of a size to permit a continuous flow of fluid therethrough. As seen in FIG. 2 and actue angled taper 72 is provided to leave a relatively sharp, rounded edge 15. The shape, length, and dimensions of the tool member may vary depending upon the type of mass or cataract to be removed.

The fluid supply means may include the container or reservoir 75 of the intravenous type that is being suspended from a handle 76 that is supported by means of a support arm or hook 78 which is coupled to a support surface 80. From the front end 82 of the reservoir 75 extends a tubular member 84 connected by a rear coupling member 85 to a front coupling member 86 which in turn is connected to a tube and fitting 90 such that the fluid 22 may flow therethrough and into the tool member 14 from an exterior source. Mounted on the tubular member 84 is a stop cock or valve 87 having a control knob 89 to control the fluid rate through the tubular member 84. Although not shown, if so desired, the fluid may be supplied directly through the instrument and through the tool.

The coupling members 85 and 86 are in two sections adapted to be removably coupled to each other and as seen in FIG. 2, the tube 88 at its lower end 92 is in telescopic relationship to the rear end 94 which has a shoulder 95 secured in a fluid tight manner as by soldering or brazing to the rear surface 52 of the shank 48. The passageway 96 connects with the bore 60 of the tool member 14 to permit a continuous flow of fluid to the operative site.

PROPOSED THEORY OF PRESENT INVENTION

Whereas a scientific explanation of the theory based on observation of the phenomena involved is disclosed below, it is to be clearly understood that the invention is by no means limited by any such scientific explanation.

The use of the instrument of the invention as applied to cataract removal is illustrated in FIGS. 3–15. A portion of a simplified cross section of a human eye 100 is shown to illustrate the manner in which the device is employed. The opaque lens or cataract which is to be broken apart and removed to is designated by the numeral 102 and is encased in a membrane having a rear portion 105 known as the posterior capsule. The iris is designated by the numeral 106 and the major gel-filled portion of the eye, or vitreous, is shown at 108. The cornea, the transparent outer surface of the eye, is shown at 110.

To avoid having to pierce or cut the iris, suitable drugs are administered to dilate the iris to its maximum extent, so that as much of the anterior capsule 102 is exposed as is possible. A small incision 112 is then made in the transparent cornea as far as possible from the center of the pupil area. This incision is made initially only about 1 to 3 mm. in length to provide access for a knife to enter the anterior chamber for removal of the anterior capsule. After the capsule is removed, the incision is enlarged to 2–12 mm., usually 4–6 mm., to provide proper access for the operative tip of the vibratory assembly.

Figure 3:
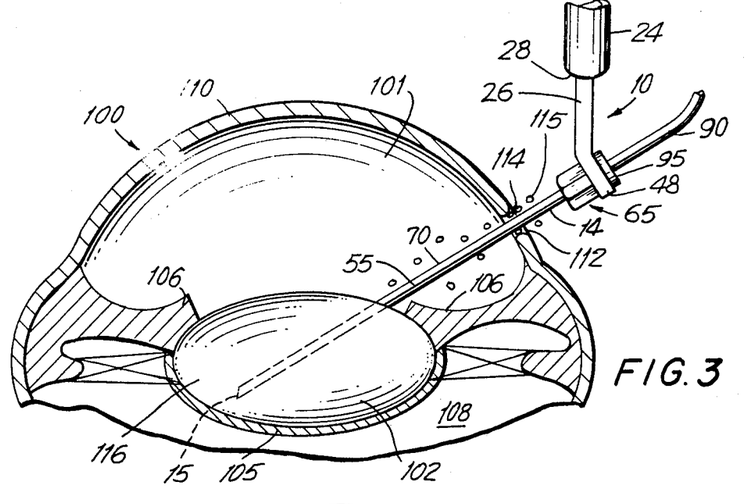
FIG. 3 is a greatly enlarged section of a portion of the human eye illustrating the insertion of the tool member in accordance with the invention.
Figure 4:
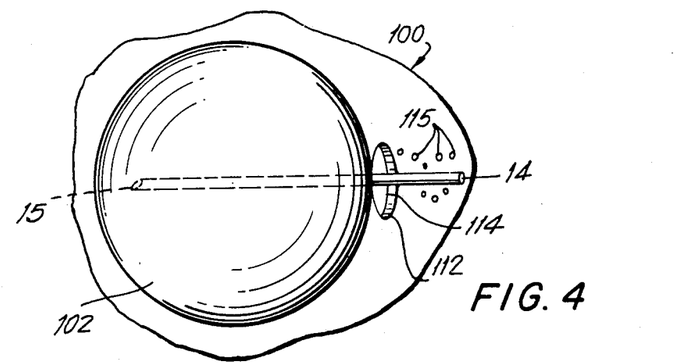
FIGS. 4-9 are greatly enlarged diagrammatic views to help illustrate the theory of the present invention with respect to the removal of the mass.

After the capsule is removed with a surgical instrument, as indicated in FIG. 3, the corneal incision is enlarged, and the operative tip is inserted into the body of the cataract 102, whereby the lens tissue mass is broken apart into minute particles. During this portion of the operation, a supply of irrigating fluid is flowing continuously through the operative tip 15 while the transducer is energized periodically for very short intervals of time.

Accordingly, applicant has discovered that cataracts which exist in an enclosed area in an animal may be removed with ultrasonic energy when a tool having a relatively sharp output edge is inserted in an incision having a width of approximately 0.040 inch and vibrating the tool ultrasonically such that as one progressively engages the cataract material that there is a reduction in the size thereof until sufficient room or space between the outer surface 70 of the tool member 14 and the width of the incision 112 to permit the reduced mass or portions of the cataract to flow outwardly therefrom without the need of *any* suction forces or any mechanical means to be utilized with respect thereto.

As the procedure of cataract removal takes place, the treatment fluid 22 as seen in FIG. 1 from the treatment fluid supply means enters the work site 116, to keep the eye inflated, by gravity feed. Although the fluid is shown as delivered through the tool 14 it may be so delivered by a separate tube in a spaced apart relation to the tool member 14 or in a tube co-axially mounted within or against the tool member 14 from the same or different incision. For the average human cataract operation the tool member may be within the anterior chamber with lavage occurring from about 1 minute to 45 minutes with treatment fluid in the range of 50cc to 1,000cc used. During this time the aggregate total time of vibration of the tool member may be from 5 seconds to 5 minutes, but applied on an intermittent basis. In this way, since the gravity feed is open to atmospheric pressure at one end of the system and the incision 112 is also opened to atmospheric pressure, there are no mechanical means for either pumping materials from the working site 116. Therefore, applicant's invention is the ultimate in simplicity in has ability to perform a surgical procedure with ultrasonic energy without the need of any forms of mechanical pumping or suction as compared to the prior art. Obviously, this extremely simplifies and evolves into the novel apparatus and method of the present invention.

Accordingly, the treatment fluid 22 is supplied from the reservoir 75 of a chemical solution of appropriate type and suitable for its intended use. The fluid also acts to keep the anterior chamber hydraulically inflated to maintain its shape during the surgical procedure. The switch 40 provided is to enable the control of the generator 30 such as to permit the user appropriate control during the surgical procedure. The switch 40 may be of any convenient type, preferably resting on the floor so as to permit the user to be able to use his foot to actuate same thereby permitting both hands of the user free to perform the necessary operation.

The instrumentation 12 is used for the removal of an object or substance which is generally of a combined mass of undesired tissue located within the region of healthy tissue below the skin. To remove the tissue which is in the form for purpose of discussion a cataract, 102, initially, the small surgical incision 112 is made through the cornea adjacent to the enclosed cataract mass 102 to enable the operative output edge or tip 15 of the handpiece 12 to reach the tissue mass 102. As the output edge of the tool member 14 is inserted through the incision 112 and into contact with the unwanted tissue, the surgeon actuates the switch 40 to power the generator and in turn the ultrasonic motor 45 is vibrated and the high frequency mechanical vibrations are transmitted to the tip 15.

Figure 5:
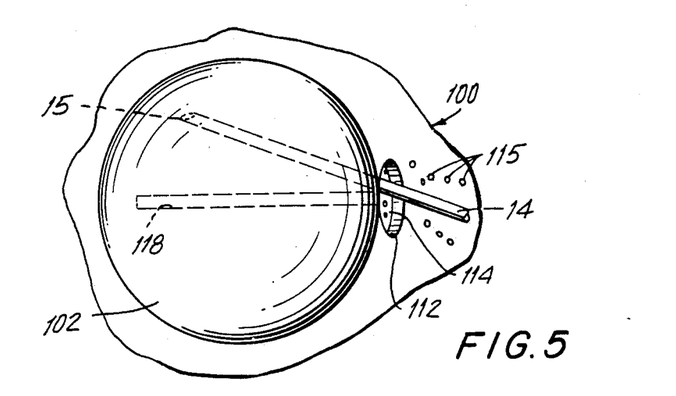

At the same time the treatment supply means 20 in its open position such that as the operative tip 15 of the tool member 14 is brought into contact with the mass 102 the operative tip 15 vibrates at a high frequency rate and with a small amplitude against the tissue mass 102 and concurrently, the treatment fluid supply 22, which is preferably selected of a type that is compatible with the animal tissue being treated such as saline fluids, bathes the work site region 116 at the tip 15 and which is being subjected to the vibratory motion. The surgeon having attained this status is now ready to commence the cataract removal technique developed by applicant in that the surgeon initially allows the ultrasonic to essentially pull the tip 15 into the mass 102 a defined length which is related to the size and hardness of the cataract and as seen particularly in FIGS. 3 and 4, an initial bore or aperture 118 as seen in FIG. 5 is formed into the cataract 102 and at that instant, it is believed certain amount of particles 115 tend to be broken away or shattered from the cataract 102 and these particles 102 flow into the anterior chamber 101 and thereafter find their way along the tool shank 55 and exit from the incision 112 as the fluid is continued to be supplied through the tool member 14. As this initial aspect of the process takes place, the work site 116 continues to be flooded or bathed with the treatment fluid and as the ultrasonic energy engages the cataract 102 then at the operative site 116, particles 115 of removed tissue in the treatment fluid and the particles 115 exit from the incision 112. The unwanted tissue thus separated from the cataract body is removed as it is broken apart and the effect of the initial bore is to in effect reduce the mass of the cataract.

Figure 6:
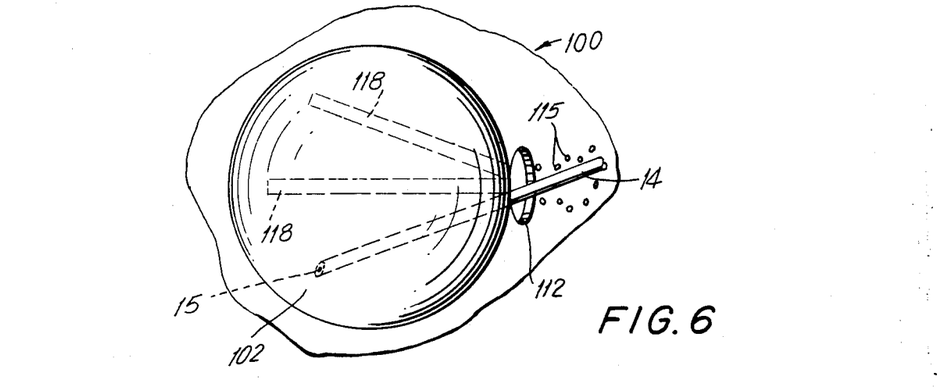
Figure 6A:
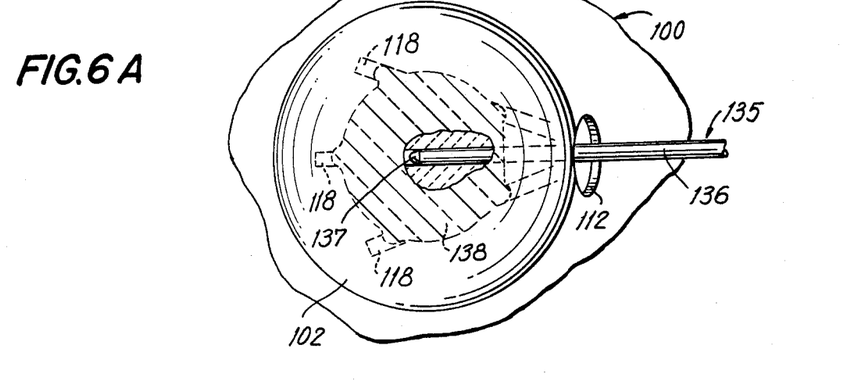
Figure 6B:
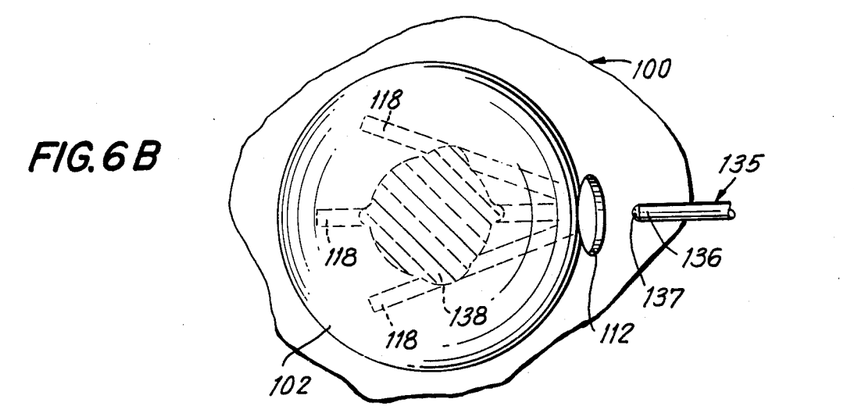
Figure 6C:
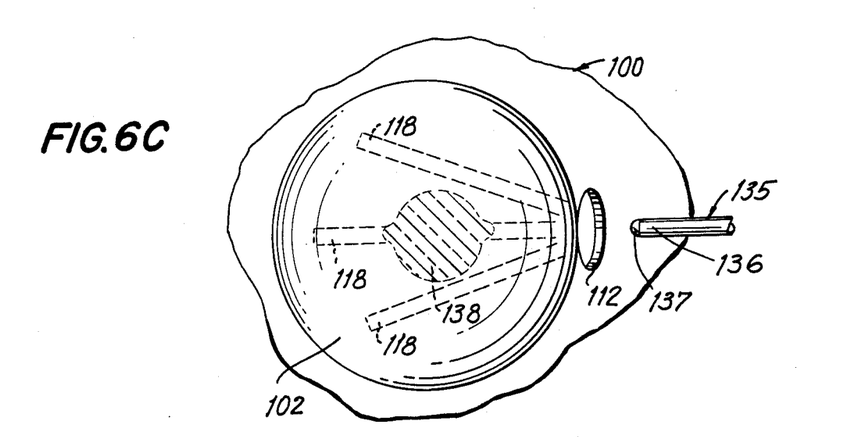

The surgeon then retracts the tool member 14 from the cataract 102 but not the incision 112 and as seen particularly in FIG. 5, thereafter drills a second bore 118 while the cataract is essentially fixed in position. Although other incisions may be made so that the tool may be inserted into the cataract from the other areas, the basis of using a single incision is to have minimal traumatic shock to the patient so as to minimize his recovery time. Accordingly, as seen in FIG. 5 and thereafter in FIG. 6, the two additional bores 118 are formed into the cataract mass 102 which in effect causes a reduction in volume of the total mass and a shrinking of the size of the cataract such that in a sense it may be angularly rotated in the direction of arrow 120 to expose another portion of the cataract 102 to the incision 112. With particular reference to FIGS. 6A, 6B, and 6C, applicant has now discovered that it is possible by first freezing and thereafter defrosting that the body of the cataract 102 may be sufficiently softened such that when the ultrasonic energy is transmitted by the operative tip while the transducer is energized periodically, that the lens tissue mass is more easily broken apart, or fractured, into minute particles. Although the discussion of FIGS. 6A–6C is contained after the aperture 118 is formed ultrasonically it is appreciated that the same may occur prior to the steps illustrated in FIGS. 3–5 and that the aperture for receiving the freezing means 135 may be formed by other means. In certain cases the freezing step may include reinserting the probe into the other apertures 118 of the lens 102 to obtain a freezing of the lens throughout.

The theory as to what actually occurs internally in the lens is not totally understood by applicant but it is believed that upon freezing and thereafter defrosting, there is an uptake of the fluid within the lens and upon its release upon defrosting does cause a softening of the nucleus of the lens 102 such that it is possible to more easily treat the hardened cataract with the ultrasonic vibratory energy. Prior to the present invention cryogenic technique in the field of cataract removal has been used for the complete opposite of what applicant is using his cryogenic technique for and that it was used to freeze the cataract or lens in situ and thereafter remove the cataract lens as one large mass in its frozen condition with no thought or concept or purpose in defrosting. What applicant has now discovered is that the defrosting has a softening effect lending itself for subsequent treatment by vibratory energy with the tool member 14 so that a hard cataract can be brought within applicant's ultrasonic surgical procedure. Accordingly, what has resulted here by applicant's discovery is an expanded use of the ultrasonic procedure particularly as related to senile cataracts.

Accordingly, by the present invention, applicant has now discovered that a change in the consistency of the lens cataract can be accomplished such that it is sufficiently softened by first freezing and thereafter unfreezing to lend itself to the ultrasonic processes of fracturing the lens such that a plurality of particles are formed of a size capable of exiting through the incision. FIGS. 6A–6C inclusive illustrate the method in which the eye 100 has the incision 112 formed therein and the freezing means 135 which may be in the form of a cryogenic probe 136 having an exposed tip 137 is inserted through the incision and in such a way there is a freezing of the mass of unwanted tissue which in this instance is the lens 102 of the eye and thereafter there is a defrosting of the mass or lens such that there is in effect a change in the structural relationship of the lens itself to cause a softening thereof.

Accordingly, as seen in FIG. 6A there is initially an engaging of the cryogenic probe 136 against the lens mass 102 for a period of time sufficient to freeze the lens and thereafter as seen in FIG. 6B, there is a removing of the cryogenic probe 136 from engagement with the lens 102. Access is gained to the lens 102 through the incision 112 and it is through this incision that the cryogenic probe 136 is inserted and removed. Initially the incision 112 is formed having a length of approximately 2–3mm in length such that there is no escape of the aqueous humor of the eye as the freezing and unfreezing process is taking place. The incision 112 is increased in length to approximately 5mm after defrosting of the lens 102 such that it permits the tool member 14 to be inserted therein and may have room for the particles of the lens as they are separated from the lens to exit in the opening defined between the incision 112 and the tool member 14.

Therefore, the ultrasonic cataract removal procedure includes the use of freezing means 135 to effect a freezing of the lens in a manner that as seen in FIG. 6A an iceball 138 is formed starting at the center or nucleus of the lens and expands outwardly until it reaches the outer limits of the nucleus or of the lens 102. It is important at that point that the freezing of the lens be stopped so that the iceball does not spread to encompass the posterior capsule of the eye. To accomplish this freezing, the cryogenic probe 136 is maintained within the lens, as by insertion in the aperture 118, for approximately 10 to 60 seconds and it has been found that generally up to 30 seconds of contact with the lens is more than sufficient to effect the freezing of the nucleus of the lens as hereinabove discussed. Accordingly, we first have the forming of one or more apertures 118 within the lens 102 which may be done with the ultrasonic tool member 14 or by some other means and thereafter the inserting in this aperture 118 of the freezing means 135 in the form of a cryogenic probe 136 and maintaining the cryogenic probe 136 within the aperture 118 for a period of time which is generally up to 30 seconds. As the cryogenic probe 136 is in contact with the lens 102, there is a maintaining of the temperature of the cryogenic probe tip 137 in a temperature range to effect a freezing of the lens. This temperature range is generally between −50° F and 0° F. Generally, it has been found sufficient if the cryogenic probe tip 137 is at a temperature of approximately −40° F, if the contact between the tip 137 and the lens 102 is maintained for the period of time indicated; however, after defrosting of the lens 102 the cryogenic probe is removed from its intimate contact with the lens. The freezing may be further continued by reinserting the probe 136 within the other apertures 118.

The change in internal structural relationship of the fibers or the actual tissue comprising the lens has been found by applicant to change upon the defrosting of the lens back to approximately room temperature. The period of time under normal operating conditions is between approximately one minute to four minutes for the defrosting to occur. During this period of time, there is in effect an uptake of the fluid into the lens which causes a softening thereof making it more suitable to treatment by ultrasonic vibratory energy. In order to obtain the hardened lens into a softened condition, the step of freezing and defrosting has been found in certain instances for certain lenses to require that it be repeated and applicant has found that repeating of the freezing and thereafter defrosting of the lens may be repeated from one to four times before the lens is sufficiently softened so that the process as hereinafter discussed with respect to FIGS. 7–15 may be continued for the removal of the lens from the eye.

At the point that the surgeon determines that the lens is sufficiently softened to continue a surgical procedure, the incision 112 may thereafter be enlarged to approximately 5mm in length so that as the particles of the lens separate from the body thereof, they may have space in which to properly exit from the eye 100. Accordingly, as seen in particular with respect to FIG. 6B, the iceball 138 starts to, in effect, melt or defrost and the probe 136 is removed through the incision 112 from the eye 100. FIG. 6C illustrates in the same time sequence of events that the lens 102 has now absorbed the fluid and begins to soften from the hardened lens to a softer and more pliable lens which can be more eaily removed. Since the surgeon is performing these steps under a microscope, he will visually see when the iceball is formed and can properly monitor equipment as to determine if the freezing and defrosting steps should be repeated and the number of times that is to occur before the final aspects of the operative procedure is to be completed.

Accordingly, the surgeon conducting the operation will have in his command the ability to form one or more frozen masses or iceballs 138 adjacent to a single aperture 118 or more than one aperture 118. For example, the surgeon may first drill three apertures as seen in FIG. 6 thereafter insert the probe 136 into one aperture and find that that area of the lens is sufficiently soft that freezing is not required. After making this decision he may then retract the probe 136 or other instrument that is used in determining how hard the lens 102 is. He may thereafter insert the probe 136 in the second aperture which area of lens is found to be sufficiently hard to warrant the freezing thereof and thereby the freezing and defrosting steps may be accomplished as discussed above. Thereafter if it is found that the area of lens 102 is still sufficiently hard the surgeon may repeat within the same aperture 118, the freezing and unfreezing process. To date, it has been found that the repeating of the freezing and unfreezing has been required in certain instances up to four times in order to accomplish the softening of the lens.

Depending upon the consistency of the lens it is appreciated that the actual iceball 138 may be contained within the immediate area of the aperture 118 that has a probe therein. Such that in effect, sequentially the probe is inserted in the first aperture 118 with the freezing and defrosting steps occurring one or more times and then perhaps into a second aperture and then into a possible third aperture with the steps of freezing and defrosting taking place one or more times. The above discussion merely indicates that there is an interrelationship between the hardness of the lens and its other internal characteristics that are determined during the medical procedure.

In employing the instrument as shown in FIG. 1, the surgeon can easily manipulate the handpiece 12 as required to work in the operative site 116 until the cataract is broken apart or is deformed so as to flow itself through the incision 112 and removed therefrom. If necessary, additional small incisions may be made at various other surface points to permit ready access to the mass 102 of unwanted tissue. However, each of these incisions need be only sufficiently large to permit the slender operative tip of the instrument to enter. The smaller the number of incisions made, the less will the trauma be and therefore the shorter the recovery time as compared to a massive excision by other procedures.

Figure 7:
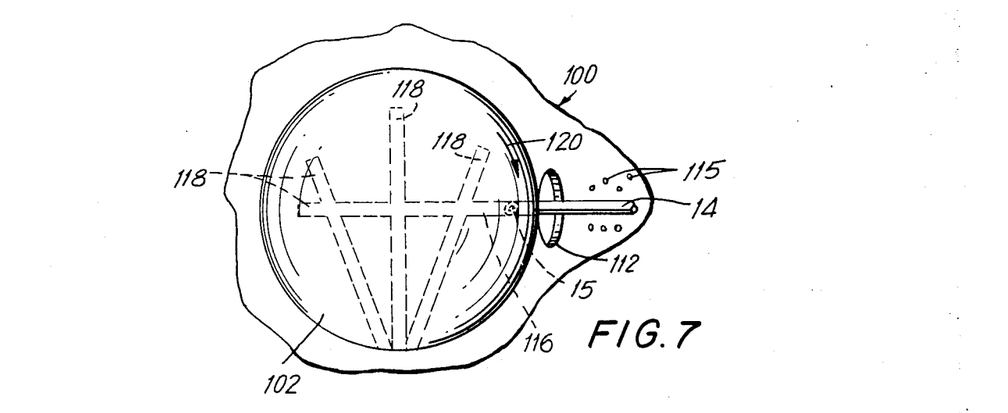
Figure 8:
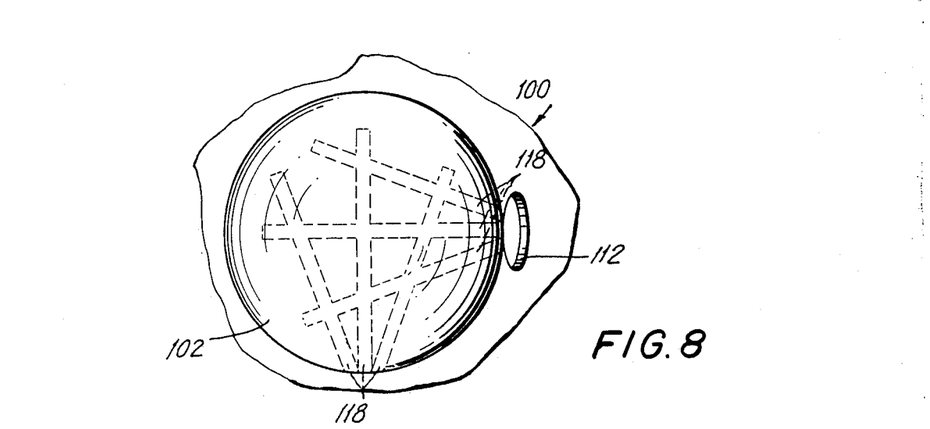

As seen with respect to FIG. 6, the third bore 118 is being formed by the surgeon and thereafter the cataract 102 due to its reduced mass tends to shrink away from its surrounding walls and is free to be rotated as illustrated by arrow 120 in FIG. 7; i.e., 90°, in the plane as seen in FIG. 3. The surgeon thereafter angularly rotates the cataract 102, if necessary, through a specific angle as particularly seen in FIG. 7, this is illustrated at approximately 90°. The physical rotation of the cataract may be conducted with the tip 15 of the tool 14, the fluid flow, or with another surgical instrument elected by the surgeon. Once the completion of the angular rotation has been accomplished, the the surgeon may thereafter commence the drilling of additional bores 118 as seen particularly in FIG. 8 where three additional bores are illustrated.

Figure 9:
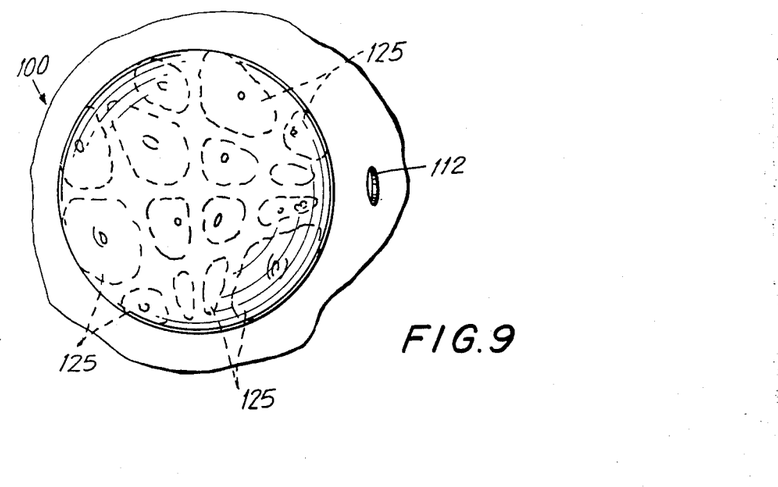

Once the cataract has had two, three, or four bores 118 therein, there is a reduction in the volume due to the amount of tissue removed and for a harder cataract a weakening of the structure and as seen diagrammatically in FIG. 9, there is formed in a sense a plurality of masses or sub-masses 125, which may be large relative to the size of the particles 115 after being subjected to ultrasonic mechanical vibrational energy, and now the task remains of in effect reducing these larger masses 125 into particles 115 which form the remains of the cataract 102. These masses 125 are removed substantially intact or the surgeon can continue to operate the tool member 14 through the opening 112.

As seen particularly in FIG. 9, the result of this crossboring or drilling through the cataract in effect reduces the cataract into a plurality of sub-masses or larger particles 125 which are generally each too large to fit between the spacing defined by the outer surface 70 of the tool 14 and the incision 112. Therefore, we are left for the moment with a number of sub-masses 125 that the surgeon now has to remove from the operative site in order to complete the surgical procedure. Since no suction is necessarily utilized, the surgeon then has the task of reducing the sub-masses 125 to particles 115 for their removal. To perform this, the surgeon positions the tip 15 of the tool member 14 against a sub-mass 125 and energizes the tip 15 to the point such that it vibrates and the vibratory energy is then transmitted to the sub-mass 125, in effect tapping it at a rate of 30,000 cycles per second such that this continuous series of blows or tapping by the mechanical tool causes a further fracturing of the sub-particle 125 such that it may be reduced to the form of a particle 115 which particles thereafter are capable of exiting in the fluid bath created from the incision 112. This fluid bath continues to fill the anterior chamber 101 and they flow therein until engaged with the ultrasonic mechanical vibrations so that their size is reduced and thereafter exit from the incision 112. In this manner, the surgeon may progressively, while working under a microscope, reposition the tool to abut or contact a mass and as same is positioned, is energized, through the switch, the vibratory tip 15 is vibrated for effecting further breaking down of each mass 125 into a particle size 115. By maintaining the fluid supply under atmospheric pressure, such that it has a gravity feed under a hydrostatic pressure produced by a fluid column, then there is a continuous flushing away that is generated such that the particles 115 once broken away from the sub-mass 125 or mass 102 tend to be carried in this fluid stream that is created always flowing towards the incision 112 from which the fluid is exiting. Since the particles do not have to exit through the tool member 14 then the tool may be maintained at a relatively small diameter, generally in the range of 0.030 in. to 0.050 in. In review, then, FIGS. 3–10 illustrate the basis by which there is initially a forming of several bores through the cataract from the singular incision until the cataract mass has been sufficiently reduced in size and therefore is freely rotatable and thereafter due to the additional bores created there may be essentially a fracturing of the cataract into a number of smaller sub-masses. The actual fracturing is somewhat dependent upon the hardness of the cataract and for a softer cataract it is appreciated that the actual removal process is somewhat different than for a harder cataract. In particular for a softer cataract the initial drilling is performed as illustrated in FIGS. 3–6 in order to obtain a reduction of the site or volume of the mass 102 in its enclosed area in the eye. Then the removing of the mass 102 of reduced volume occurs essentially intact through the incision as seen in respect to FIGS. 11–13. Thus for a soft cataract the individual sub-masses as seen in FIG. 9 need not be formed.

Figure 10:
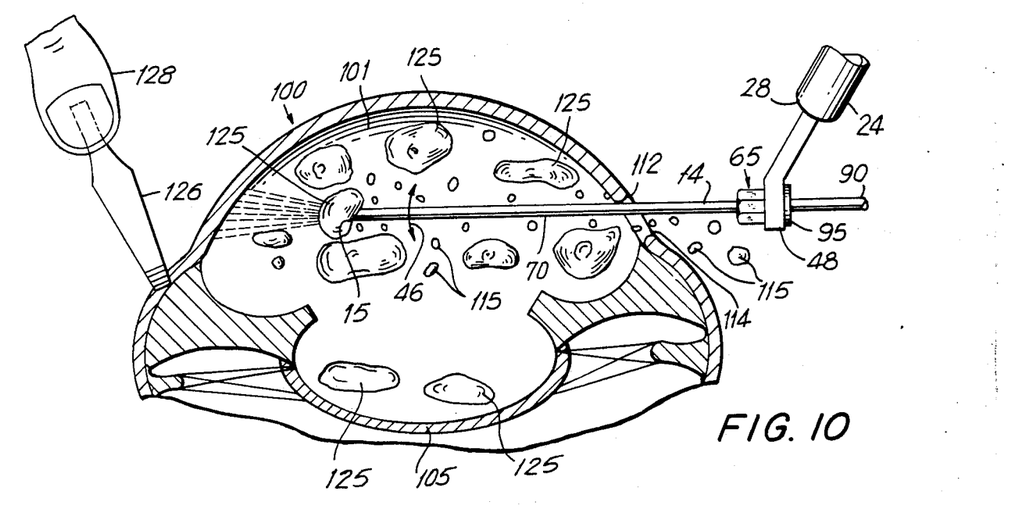
FIG. 10 is a diagrammatic view similar to FIG. 3 illustrating the process of removing the respective masses.

During the surgical procedure as illustrated in FIG. 10, the incision 112 is maintained in an open state by the surgeon applying the necessary force by gripping the appropriate portion of the eye with the tweezer 106 as the surgeon 128 applies the necessary force to maintain the open position of the incision 112.

Figure 11:
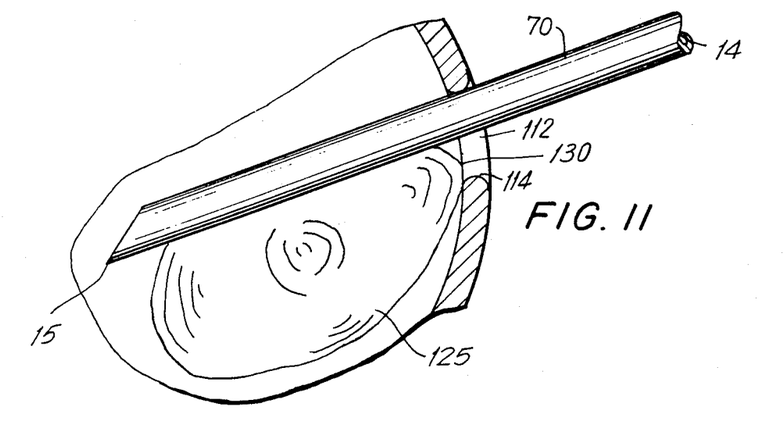
FIGS. 11-15 are greatly enlarged diagrammatic views to illustrate the exiting of each mass or particle from the incision.
Figure 12:
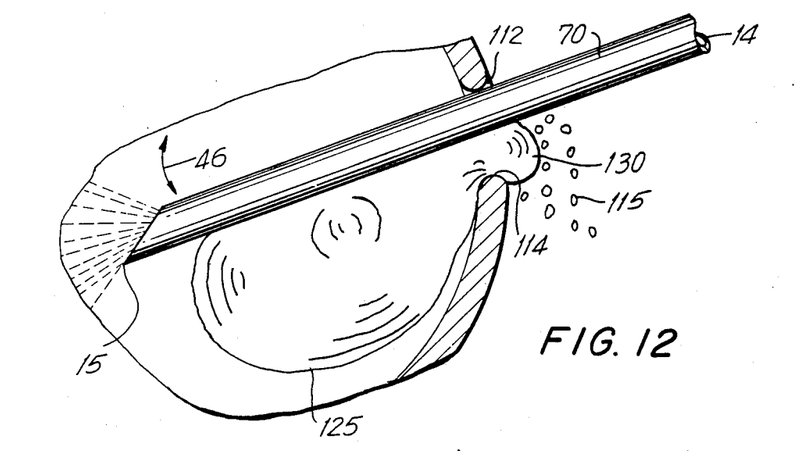
Figure 13:
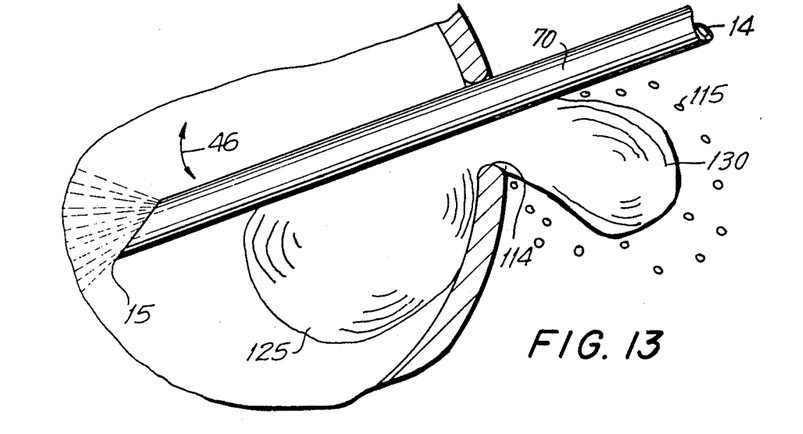
Figure 14:
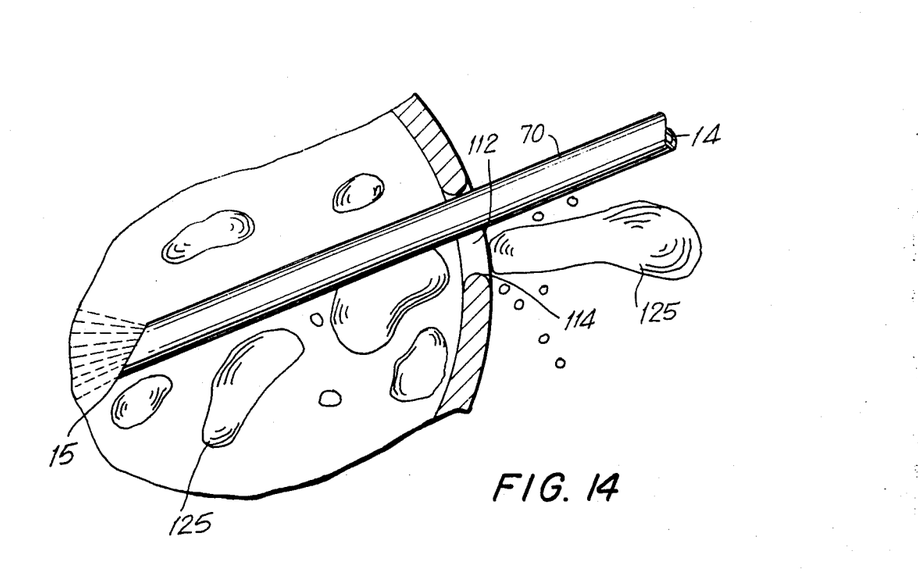
Figure 15:
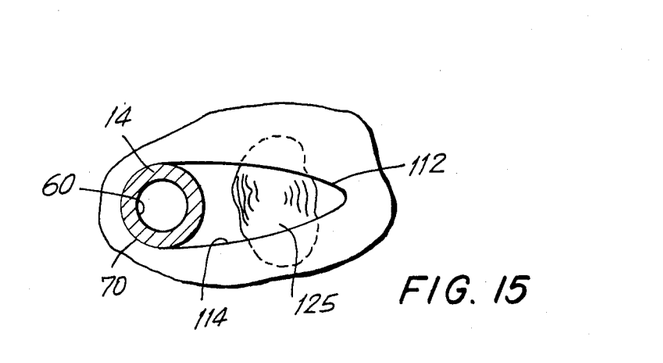

As seen in FIGS. 11, 12, 13, and 14, a novel aspect of the present invention is seen in the ability of particles 115, sub-masses 125, or cataract mass 102 which have a larger volume or cross-section than the space defined between the outer surface 70 of the tool member 14 and the incision 112 to escape therethrough. What has been noticed is the ability of the mass to more or less squeeze its way out of an opening by changing its width in the constricted area between the incision wall 114 and the tool member 14. Since the particle is not of a completely hard surface that has no flexibility, there is this "wiggling," shrinking or moulding at its respective section which as seen in FIGS. 11–14 is progressive such that it creeps out through the opening 112 and carried in the fluid flow that has been created in the area. Initially with respect to the progressive steps illustrated in steps 11–14, the sub-mass 125 due to the fluid flow initially positions itself such that its leading edge 130 abuts the incision 112 while the tool member 14 is not vibrated. The complete removal of the mass may occur without any vibration because of the pressure within the anterior chamber by the fluid flow. Also the surgeon viewing the sub-mass 125 reaching the position as seen in FIG. 11 through the microscope may energize the circuitry such that the tip 115 starts to vibrate as indicated by arrow 46 such that there is what is believed to be a viscosity reduction effect or reduction of friction effect a known phenomena of ultrasonic mechanical vibrations such that between the outer of surface 70, the tool member 14 and the incision wall 114, the leading edge 130 of the sub-mass 125 continues its creeping "motion" until it progressively exits from its captivity as seen in FIG. 13 and thereafter as seen in FIG. 14 has fully left the confines of the eye. This step is repeated until the other masses 125 which cannot freely exit from the eye are freed of their captivity.

CONCLUSION

It will be apparent from a reading of the disclosure herein that a novel and improved surgical procedure for first softening and thereafter breaking apart and removing of tissue, such as a cataract, has been developed and that same may be rapidly removed with a minimum of damage to surrounding tissue. The present novel improved process and equipment provides a surgical procedure for the safe removal of cataracts by first softening the lens and thereafter reducing the volume and removing it by breaking it apart into minute particles and removing them rapidly from the operative site. It is seen that the apparatus and procedure is simplified to the extent that no mechanical suction or pressure is required in order to operate and therefore the possibility of damage due to the malfunction of any equipment does not exist in the present process.

Although the invention has been illustrated with respect to the removal of cataracts, it is appreciated that other objects that are to be removed may also be removed in the same surgical procedure from a human and other bodies and that the use of the cataract is merely intended for illustrative purposes and the invention is not at all limited with respect thereto.

Therefore, it is not desired that the invention be limited to the specific details illustrated and described and it is intended by the appended claims to cover all modifications which fall within the spirit and scope of the invention.

I claim:

1. The method of removing a mass of unwanted tissue from an enclosed area in an animal with a tool member having an output edge, comprising the steps of:
   A. forming an incision in an area proximate to the mass of unwanted tissue,
   B. freezing the mass of unwanted tissue,
   C. defrosting the mass of unwanted tissue,
   D. reducing the size of the mass in its enclosed area by engaging the output edge of the tool member against the mass and ultrasonically vibrating the output edge, and
   E. removing the reduced mass from the incision.

2. The method as defined in claim 1, wherein the step of freezing said mass includes the steps of:
   a. engaging a cryogenic probe against said mass for a period of time sufficient to freeze said mass, and
   b. removing said cryogenic probe from engagement with said mass.

3. The method as defined in claim 2, and further including the step of inserting said cryogenic probe through said incision for engaging said mass.

4. The method as defined in claim 2, and further including the step of forming an aperture within said mass; and wherein said cryogenic probe is positioned within said aperture for freezing thereof.

5. The method as defined in claim 1, and further including the step of increasing the length of said incision until it reaches approximately 2 to 3 millimeters.

6. The method as defined in claim 1, and further including the step of increasing the length of said incision prior to the step of reducing the size of the mass.

7. The method as defined in claim 6, and further including the step of increasing the length of said incision to approximately 5 millimeters.

8. The method as defined in claim 1, wherein the step of freezing said mass includes the steps of:
   a. forming an aperture within said mass,
   b. inserting in said aperture a cryogenic probe,
   c. retaining said cryogenic probe within said aperture for a period of time,
   d. maintaining the temperature of said cryogenic probe in a temperature range to effect a freezing of said mass, and
   e. thereafter removing said cryogenic probe from said mass.

9. The method as defined in claim 8, wherein said cryogenic probe is maintained within said mass for approximately 10 to 60 seconds.

10. The method as defined in claim 8, wherein said cryogenic probe is maintained in the temperature range between −50° to 0° Fahrenheit.

11. The method as defined in claim 1, wherein said mass is reduced in size by forming a plurality of apertures in said mass from varying directions with the tool member ultrasonically vibrated.

12. The method as defined in claim 11, wherein said plurality of apertures effect a separating of the mass to form a plurality of masses for removal from the incision.

13. The method as defined in claim 1, and further including the steps of freezing and defrosting the mass one or more times.

14. The method as defined in claim 1,
   a. and further including the steps of supplying a fluid in the area of said mass, and
   b. removing said mass through the incision as said supply of fluid is introduced in the area of said mass.

15. The method as defined in claim 14, and further including the step of supplying said fluid through the tool member.

16. The method as defined in claim 1, and further including the step of pressing the tool member against one end of said incision to obtain the maximum opening of the incision so as to permit the mass to exit through the incision.

17. The method as defined in claim 16, and further including the step of permitting the mass to abut the incision from the inner surface during a period when the tool member is not vibrating and thereafter vibrating the tool to cause the mass to exit through the incision.

18. The method as defined in claim 1, and further including the step of supporting the area adjacent the incision to maintain the incision in an open position during the exiting of the mass therefrom.

19. The method as defined in claim 1, and further including the step of laterally vibrating the output edge of said tool member.

20. The method as defined in claim 1, and further including the step of vibrating said tool member in the frequency range of 5KHz to 50KHz.

21. The method of removing a mass of unwanted tissue from an enclosed area in an animal with a tool member having an output edge, comprising the steps of:
A. forming an incision in an area proximate to the mass of unwanted tissue,
B. freezing the mass of unwanted tissue by means of:
1. forming an aperture within said mass,
2. inserting in said aperture a cryogenic probe,
3. retaining said cryogenic probe within said aperture for a period of time,
4. maintaining the temperature of said cryogenic probe in a temperature range to effect a freezing of said mass, and
5. thereafter removing said cryogenic probe from said mass,
C. defrosting the mass of unwanted tissue,
D. increasing the length of the incision,
E. reducing the size of the mass in its enclosed area by engaging the output edge of the tool member against the mass and ultrasonically vibrating the output edge,
F. supplying a fluid to the area adjacent the vibrating tool member, and
G. removing the reduced mass from the incision.

22. The method as defined in claim 21, and further including the steps of inserting and removing said cryogenic probe through said incision.

23. The method as defined in claim 21, and further including the step of increasing the length of said incision until it reaches approximately 2 to 3 millimeters.

24. The method as defined in claim 21, and further including the step of increasing the length of said incision to approximately 5 millimeters.

25. The method as defined in claim 21,
a. and further including the steps of supplying a fluid in the area of said mass, and
b. removing said mass through the incision as said supply of fluid is introduced in the area of said mass.

26. The method as defined in claim 21, and further including the step of supplying said fluid through the tool member.

27. The method as defined in claim 21, and further including the step of maintaining said cryogenic probe within said cataract for approximately 10 to 60 seconds.

28. The method as defined in claim 21, and further including the step of maintaining the temperature of said cryogenic probe in the range between −50° to 0° Fahrenheit.

29. The method of removing a cataract mass of tissue from its enclosed area in the eye, comprising the steps of:
A. forming an incision on the eye in order to gain access to said cataract,
B. freezing said cataract,
C. defrosting said cataract,
D. inserting a tool member having an output edge through the incision,
E. engaging the output edge of said tool member with the surface of said cataract,
F. supplying a fluid to the area adjacent the output edge of said tool member,
G. reducing the size of the cataract in its enclosed area by:
1. vibrating the tool member to provide peak accelerations of at least 1,000g, to transmit said vibrations to the tissue of the cataract in engagement therewith,
2. moving said vibrating tool member relative to said cataract to form an aperture in said cataract to reduce the volume thereof,
3. retracting said vibrating tool member from the aperture formed within said cataract, and
H. removing said cataract from the incision.

30. The method as defined in claim 29, wherein the step of freezing said cataract includes the steps of:
a. engaging a cryogenic probe against said cataract for a period of time sufficient to freeze said cataract, and
b. removing said cryogenic probe from engagement with the cataract.

31. The method as defined in claim 30, and further including the steps of inserting and removing said cryogenic probe through said incision.

32. The method as defined in claim 29, and further including the step of increasing the length of the incision until it reaches approximately 2 to 3 millimeters.

33. The method as defined in claim 29, and further including the step of increasing the length of the incision prior to the step of reducing the size of said cataract.

34. The method as defined in claim 33, and further including the step of increasing the length of said incision to approximately 5 millimeters.

35. The method as defined in claim 29, wherein the step of freezing the cataract includes the steps of:
a. forming an aperture within said cataract,
b. inserting in said aperture a cryogenic probe,
c. retaining said cryogenic probe within said aperture for a period of time,
d. maintaining the temperature of said cryogenic probe in a temperature range to effect a freezing of said cataract, and
e. thereafter removing said cryogenic probe from said cataract.

36. The method as defined in claim 35, and further including the step of maintaining said cryogenic probe within said cataract for approximately 10 to 60 seconds.

37. The method as defined in claim 35, and further including the step of maintaining the temperature of said cryogenic probe in the range between −50° to 0° Fahrenheit.

38. The method as defined in claim 29, and further including the steps of:
a. rotating said cataract to expose another portion of said cataract, and
b. reinserting said vibrating tool member into said cataract to form another aperture therein, until sufficient tissue has been removed to form a plurality of masses.

39. The method as defined in claim 36, and further including the step of progressively contacting said cataract masses by engaging the output edge of the tool member against a respective mass and energizing said vibratory output edge to further reduce the size of each mass so as to permit said respective mass to exit from the incision.

40. The method of removing a cataract mass of tissue from the eye, comprising the steps of:
   A. forming an incision on the eye in order to gain access to said cataract tissue,
   B. freezing said cataract mass,
   C. defrosting said cataract mass,
   D. inserting a tool member having an output edge through the incision,
   E. engaging the output edge of said tool member with the surface of said cataract,
   F. supplying a fluid through said tool member adjacent said cataract,.
   G. vibrating the tool member to provide peak accelerations of at least 1,000g to transmit said vibrations to the tissue of said cataract in engagement therewith,
   H. moving said vibrating tool member relative to said cataract to form an aperture in said cataract,
   I. retracting said vibrating tool member from the aperture formed within said cataract,
   J. rotating said cataract to expose another portion of said cataract,
   K. reinserting said vibrating tool member into said cataract to form another aperture therein, until a plurality of masses are formed, and
   L. progressively reducing the size of the respective masses by contacting the output edge of the tool member thereagainst and energizing said vibratory tip to further reduce the size thereof so as to permit said mass to exit from the incision.

41. The method as defined in claim 40, wherein the step of freezing said cataract includes the steps of:
   a. engaging a cryogenic probe against said cataract for a period of time sufficient to freeze said cataract, and
   b. removing said cryogenic probe from engagement with the cataract.

42. The method as defined in claim 41, and further including the steps of inserting and removing said cryogenic probe through said incision.

43. The method as defined in claim 40, and further including the step of increasing the length of the incision until it reaches approximately 2 to 3 millimeters.

44. The method as defined in claim 40, and further including the step of increasing the length of the incision prior to the step of reducing the size of said cataract.

45. The method as defined in claim 40, and further including the step of increasing the length of said incision to approximately 5 millimeters.

46. The method as defined in claim 40, wherein the step of freezing the cataract includes the steps of:
   a. forming an aperture within said cataract,
   b. inserting in said aperture a cryogenic probe,
   c. retaining said cryogenic probe within said aperture for a period of time,
   d. maintaining the temperature of said cryogenic probe in a temperature range to effect a freezing of said cataract, and
   e. thereafter removing said cryogenic probe from said cataract.

47. The method as defined in claim 40, and further including the step of maintaining said cryogenic probe within said cataract for approximately 10 to 60 seconds.

48. The method as defined in claim 40, and further including the step of maintaining the temperature of said cryogenic probe in the range between $-50°$ to $0°$ Fahrenheit.

49. The method as defined in claim 40, and further including the step of vibrating said tool member in the frequency range of 5KHz to 50KHz.

50. The method as defined in claim 40, and further including the step of first forming one or more apertures in said cataract prior to the step of freezing said cataract mass.

51. The method of softening the lens of the eye prior to removing same therefrom with ultrasonic energy, comprising the steps of:
   A. freezing the lens of the eye, and
   B. defrosting the lens of the eye.

52. The method as defined in claim 51, and further including the step of repeating said steps of freezing and defrosting until the lens is sufficiently softened for the application of the ultrasonic energy thereto.

53. The method as defined in claim 51, wherein the step of freezing said lens includes the steps of:
   a. engaging a cryogenic probe against said lens for a period of time sufficient to freeze said lens, and
   b. removing said cryogenic probe from engagement with said lens.

54. The method as defined in claim 53, and further including the step of first forming an incision in an area proximate to the lens of the eye to gain access to the lens thereof.

55. The method as defined in claim 54, and further including the step of inserting said cryogenic probe through said incision for engaging said lens.

56. The method as defined in claim 51, wherein the step of freezing said lens includes the steps of:
   a. forming an aperture within said lens,
   b. inserting in said aperture a cryogenic probe,
   c. retaining said cryogenic probe within said aperture for a period of time,
   d. maintaining the temperature of said cryogenic probe in a temperature range to effect a freezing of said lens, and
   e. thereafter removing said cryogenic probe from said lens.

57. The method as defined in claim 56, and further including the step of maintaining said cryogenic probe within said cataract for approximately 10 to 60 seconds.

58. The method as defined in claim 56, and further including the step of maintaining the temperature of said cryogenic probe in the range between $-50°$ to $0°$ Fahrenheit.

59. The method as defined in claim 51, and further including the step of repeating said steps of freezing and defrosting the lens.

* * * * *